United States Patent
Thangappan et al.

(10) Patent No.: US 10,380,747 B2
(45) Date of Patent: Aug. 13, 2019

(54) METHOD AND SYSTEM FOR RECOMMENDING OPTIMAL ERGONOMIC POSITION FOR A USER OF A COMPUTING DEVICE

(71) Applicant: Wipro Limited, Bangalore (IN)

(72) Inventors: Anandaraj Thangappan, Bangalore (IN); Jayakumar Panicker, Bangalore (IN)

(73) Assignee: Wipro Limited, Bangalore (IN)

( * ) Notice: Subject to any disclaimer, the term of this patent is extended or adjusted under 35 U.S.C. 154(b) by 23 days.

(21) Appl. No.: 15/243,994

(22) Filed: Aug. 23, 2016

(65) Prior Publication Data

US 2018/0005386 A1 Jan. 4, 2018

(30) Foreign Application Priority Data

Jun. 30, 2016 (IN) .............................. 201641022516

(51) Int. Cl.
*G06T 7/246* (2017.01)
*G06T 7/285* (2017.01)
(Continued)

(52) U.S. Cl.
CPC ................ *G06T 7/251* (2017.01); *A61B 5/11* (2013.01); *A61B 5/4561* (2013.01); *G06F 3/011* (2013.01);
(Continued)

(58) Field of Classification Search
CPC ........... G06T 7/251; G06T 7/285; A61B 5/11; A61B 5/103; A61B 5/1128; A61B 5/4561;
(Continued)

(56) References Cited

U.S. PATENT DOCUMENTS 6,592,223 B1    7/2003  Stern et al.
2001/0031451 A1* 10/2001 Sander .................... G09B 7/00
                                                     434/236
(Continued)

FOREIGN PATENT DOCUMENTS

DE    10 2013 109 830    3/2015

OTHER PUBLICATIONS

Alvaro Uribe-Quevdo et al., "Seated tracking for correcting computer work postures", 2013, 29th Southern Biomedical Engineering Conference, *IEEE Computer Society*, pp. 169-170.
(Continued)

*Primary Examiner* — Jingge Wu
(74) *Attorney, Agent, or Firm* — Finnegan, Henderson, Farabow, Garrett & Dunner, LLP

(57) ABSTRACT

The present disclosure relates to a method and system for recommending optimal ergonomic position for a user of a computing device by a recommendation system. The recommendation system receives user data from one or more data sources and extracts a profile of the user from a repository based on the user data. The recommendation system identifies one or more critical areas of the user, where each of the critical areas are associated with a plurality of pre-defined position parameters and also monitor the plurality of pre-defined position parameters of the user to determine corresponding values. The recommendation system compare the values of the plurality of pre-defined position parameters with predefined values of the pre-defined position parameters and identify deviations in one or more of the plurality of pre-defined position parameters based on the comparison and provide recommendations for correcting the deviations from the pre-defined position parameters to the user.

21 Claims, 6 Drawing Sheets

(51) Int. Cl.
*A61B 5/11* (2006.01)
*H04N 5/232* (2006.01)
*A61B 5/00* (2006.01)
*G06F 3/01* (2006.01)

(52) U.S. Cl.
CPC ......... *G06T 7/285* (2017.01); *H04N 5/23293* (2013.01); *G06T 2207/30196* (2013.01)

(58) Field of Classification Search
CPC .......... H04N 5/23293; H04N 21/25841; B60R 16/037; B60R 25/01; G06K 9/00255; G06K 9/00335
See application file for complete search history.

(56) References Cited

U.S. PATENT DOCUMENTS

| | | | | |
|---|---|---|---|---|
| 2004/0010328 A1* | 1/2004 | Carson | ............... | G06Q 10/00 700/90 |
| 2007/0083384 A1* | 4/2007 | Geslak | ............... | G06Q 10/00 705/2 |
| 2007/0149360 A1* | 6/2007 | Narayanaswami | .... | A63B 24/00 482/8 |
| 2009/0024005 A1 | 1/2009 | Lewicke et al. | | |
| 2009/0030767 A1* | 1/2009 | Morris | ............... | G06Q 10/06 705/7.18 |
| 2010/0094645 A1 | 4/2010 | Carroll et al. | | |
| 2011/0080290 A1* | 4/2011 | Baxi | ............... | A61B 5/1116 340/573.1 |
| 2013/0110004 A1 | 5/2013 | McLane et al. | | |
| 2014/0025396 A1* | 1/2014 | Horseman | ......... | G06F 19/3418 705/2 |
| 2014/0052345 A1* | 2/2014 | Tobin | ............... | B60R 16/037 701/49 |
| 2015/0142381 A1 | 5/2015 | Fitzsimmons et al. | | |
| 2016/0167607 A1* | 6/2016 | Rai | ............... | H04L 67/34 701/36 |
| 2016/0167608 A1* | 6/2016 | Rai | ............... | B60W 40/08 701/36 |
| 2016/0171637 A1* | 6/2016 | Rai | ............... | H04L 67/12 705/13 |
| 2016/0213140 A1* | 7/2016 | Koch | ............... | A47C 3/20 |

OTHER PUBLICATIONS

Extended Search Report from the European Patent Office in counterpart European Application No. 16191614.3, dated Mar. 6, 2017, 9 pages.

* cited by examiner

METHOD AND SYSTEM FOR RECOMMENDING OPTIMAL ERGONOMIC POSITION FOR A USER OF A COMPUTING DEVICE

FIELD OF THE INVENTION

The present subject matter is related in general to the field of ergonomics, more particularly, but not exclusively to a method and system for recommending an optimal ergonomic position for a user of a computing device.

BACKGROUND

Ergonomics is a scientific discipline which deals with how humans interact with the digital devices or equipment around and the ambient environment. Over a last few years, digital devices such as computers, mobile phones, laptops etc., have started to play a much more important role in our day to day lives. With a tremendous growth in the Information Technology over time, the digital devices are used at an enormous rate both at professional and personal front. Digital devices such as computers, laptops, mobiles phones etc., have become an important technology products required by everyone in daily life.

In typical computer workstations, which may be designed carefully considering the ergonomics factors, it is observed that most of the users while using the devices may still sit in improper postures or maintain poor work practices etc. For example, a user looking continuously at the computer device sitting very near to the device, repeatedly bending wrist up and down, by keeping elbow at inappropriate angle, placing mouse away etc. In the existing technologies, many materials are publicly available for suggesting the proper posture while using a digital device. However, in reality, a common user hardly knows or follows them. Also, many existing technologies provide correct sitting postures, which are based on only a few factors. In addition, a user trained in following ergonomics practices may sometime fail in doing so, resulting in health issues.

Thus, the existing techniques which provide correct sitting postures may not be efficient in determining the correct ergonomics positions for the users. These existing techniques do not consider all the factors which are crucial in determining ergonomic position. In addition, improper ergonomic practices may affect user's quality of work and most importantly may cause health disorders for instance, minimising visions, Muscles Musculoskeletal Disorders (MMD), back pain etc. Further, the existing techniques are restricted to a single device for a particular user. In case, a user starts using a different device, the existing techniques may not be able to identify the user and recommend an ergonomic position. Thus, there is a need for a system which recommends ergonomic position to a user of a device in real time.

SUMMARY

In an embodiment, the present disclosure relates to a method for recommending an optimal ergonomic position for a user of a computing device. The method comprises receiving user data from one or more data sources, extracting a profile of the user from a repository based on the user data, identifying one or more critical areas of the user based on the extracted profile and the user data. Each of the one or more critical areas is associated with a plurality of pre-defined position parameters. The method comprises monitoring the plurality of pre-defined position parameters of the user to determine corresponding values, comparing the values of the plurality of pre-defined position parameters with predefined values of the pre-defined position parameters, identifying deviations in one or more of the plurality of pre-defined position parameters based on the comparison and providing recommendations for correcting the deviations from the one or more of the plurality of pre-defined position parameters to the user.

In an embodiment, the present disclosure relates to a recommendation system for recommending an optimal ergonomic position for a user of a computing device. The recommendation system comprises a processor and a memory communicatively coupled to the processor, wherein the memory stores processor executable instructions, which, on execution, causes the recommendation system to receive user data from one or more data sources, extracting a profile of the user from a repository based on the user data, identify one or more critical areas of the user based on the extracted profile and the user data, where each of the one or more critical areas are associated with a plurality of pre-defined position parameters. The recommendation system monitors the plurality of pre-defined position parameters of the user to determine corresponding values, compares the values of the plurality of pre-defined position parameters with predefined values of the pre-defined position parameters, identifies deviations in one or more of the plurality of pre-defined position parameters based on the comparison and provide recommendations for correcting the deviations from the one or more of the plurality of pre-defined position parameters to the user.

In an embodiment, the present disclosure relates to a non-transitory computer readable medium including instructions stored thereon that when processed by at least one processor cause a recommendation system to receive user data from one or more data sources, extracting a profile of the user from a repository based on the user data, identify one or more critical areas of the user based on the extracted profile and the user data, wherein each of the one or more critical areas are associated with a plurality of pre-defined position parameters, monitor the plurality of pre-defined position parameters of the user to determine corresponding values, compare the values of the plurality of pre-defined position parameters with predefined values of the pre-defined position parameters, identify deviations in one or more of the plurality of pre-defined position parameters based on the comparison and provide recommendations for correcting the deviations from the one or more of the plurality of pre-defined position parameters to the user.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which:

Figure 1:
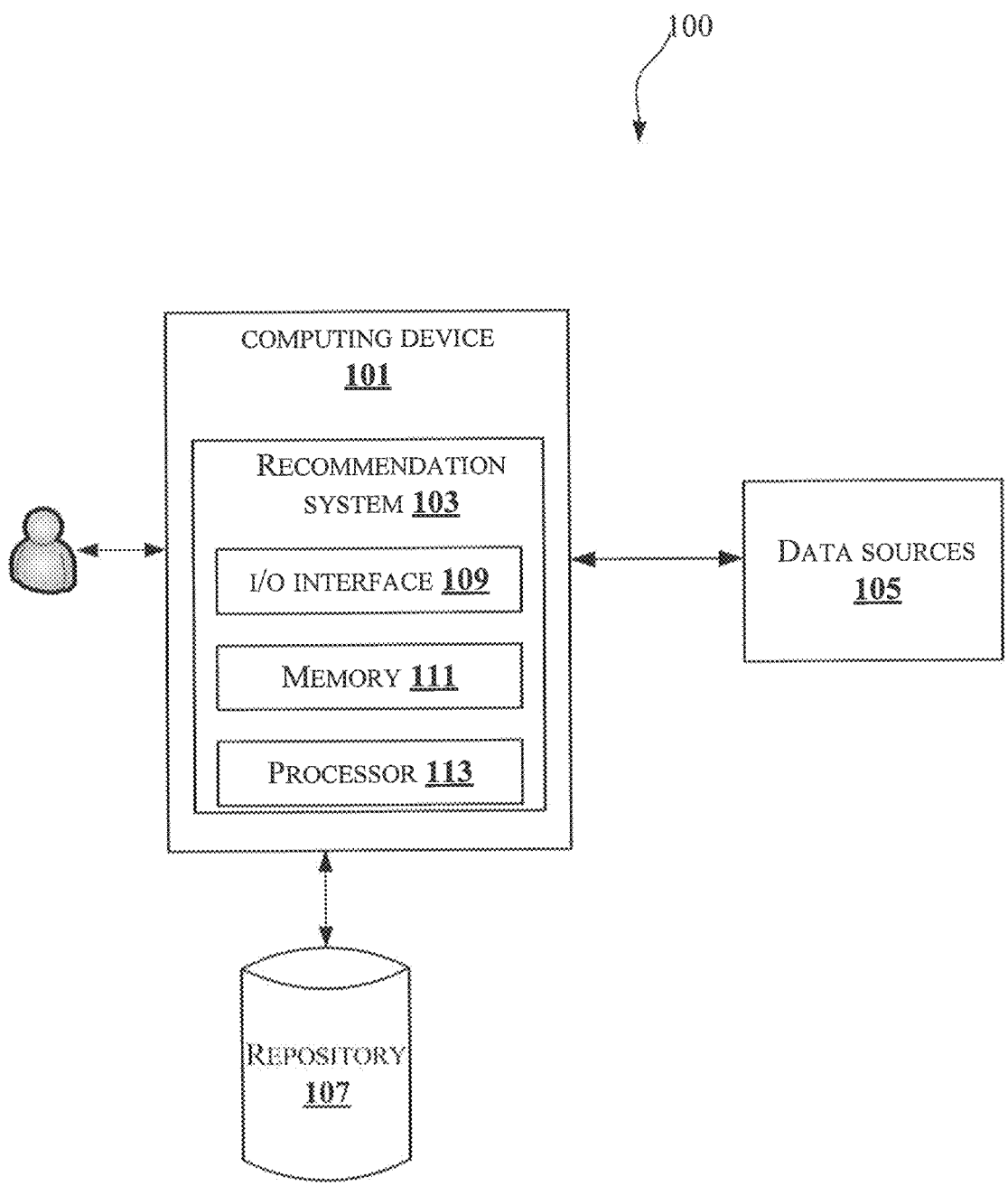
FIG. 1 illustrates an exemplary environment for recommending an optimal ergonomic position for a user of a computing device in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

The present disclosure relates to a method for recommending an optimal ergonomic position for a user of a computing device. The present disclosure provides a recommendation system which provides recommendation to the users of the computing device for correction upon identifying any deviations in pre-defined position parameters. The recommendation system monitors a plurality of pre-defined position parameters of the user of the computing device. In an embodiment, the recommendation system maintains a user profile for each of the user of the computing device, where the user profiles are utilized for identifying critical areas of the users. The present disclosure identifies any deviations in the plurality of pre-defined positions parameters of the users by comparing with the pre-defined positions parameters and provides recommendation for correcting the deviations.

FIG. 1 illustrates an exemplary environment 100 for recommending an optimal ergonomic position for a user of a computing device 101 in accordance with some embodiments of the present disclosure. As shown in FIG. 1, the environment 100 comprises the computing device 101 connected to data sources 105 and a repository 107. The computing device 101 comprises a recommendation system 103. In an embodiment, the recommendation system 103 may be present outside the computing device 101. The data sources 105 may include, but are not limited to, a video capturing unit, a depth sensor, a light sensor, a microphone, a humidity sensor and a temperature sensor. In an embodiment, the computing devices 101 include, but are not limited to, desktop computers, laptops, mobile phones, Personal Computers (PC), tablets and any other computing device. In an embodiment, the computing device 101 may comprise a display unit, a keyboard, a keypad, mouse etc. In an embodiment, a user sits in front of the computing device 101 and views the display unit. The recommendation system 103 receives user data associated with a user from the one or more data sources 105. The user data associated with the user comprises at least one of user login data, video feed from a video capturing unit and facial feature information of the user. In an embodiment, the user data is received from the computing device 101 in case the user is a registered user and the computing device 101 comprises the login details. In another embodiment, the user may also be recognized based on the facial features identified from video captured by applying facial recognition technique on captured images of the user. In addition, the facial recognition technique extracts unique features from facial images and uses them to identify the user from the set of registered users. The recommendation system 103 further extracts a profile for each of the registered users from the repository 107. The repository 107 stores profiles of the registered users. In an embodiment, a user profile is generated at the time of registration and each of the user profile is stored with a unique identifier associated with the facial feature in order to identify the user. In addition, the user profile may also comprise information about the user complete health details. In an embodiment, whenever a new user is detected in front of the computing device 101, the recommendation system 103 loads a default profile for the user. Further, based on the extracted profile of the user and the user data, the recommendation system 103 identifies one or more critical areas of the user. In an embodiment, the one or more critical areas of the user may include, but is not limited to, ears, eyes, backbone, legs, elbow etc. Also, each of the one or more critical areas of the users is associated with a plurality of pre-defined position parameters. The recommendation system 103 identifies any deviation in any of the plurality of pre-defined position parameters by monitoring the plurality of pre-defined position parameters through one or more sensors like depth sensor, light sensor, humidity sensors, temperature sensor and other data sources 105 like video capturing unit and microphone. The deviations are identified with respect to the values of the plurality of pre-defined position parameters. In an embodiment, if the user profile comprises a specific user pre-defined value for any of the plurality of pre-defined parameters, the recommendation system 103 monitors those plurality of pre-defined parameters based on the user pre-defined value. The recommendation system 103 further comprises providing deviation notification to the users, where the deviation notification comprise information about at least one of deviations of user posture, ambient lighting, temperature, sound level and humidity. In an embodiment, the deviation notifications are provided in at least one of real-time visuals form, textual form, graphical form and animated form.

The recommendation system 103 of the computing device 101 comprises an I/O Interface 109, a memory 111 and a processor 113. The I/O interface 109 is configured to receive the user data from one or more data sources 105. The I/O is also configured to receive the profiles associated with the user from the repository 107.

The received information from the I/O interface 109 is stored in the memory 111. The memory 111 is communicatively coupled to the processor 113 of the recommendation system 103. The memory 111 also stores processor instructions which cause the processor 113 to execute the instruction in order to recommend an optimal ergonomic position for a user of a computing device 101.

Figure 2A:
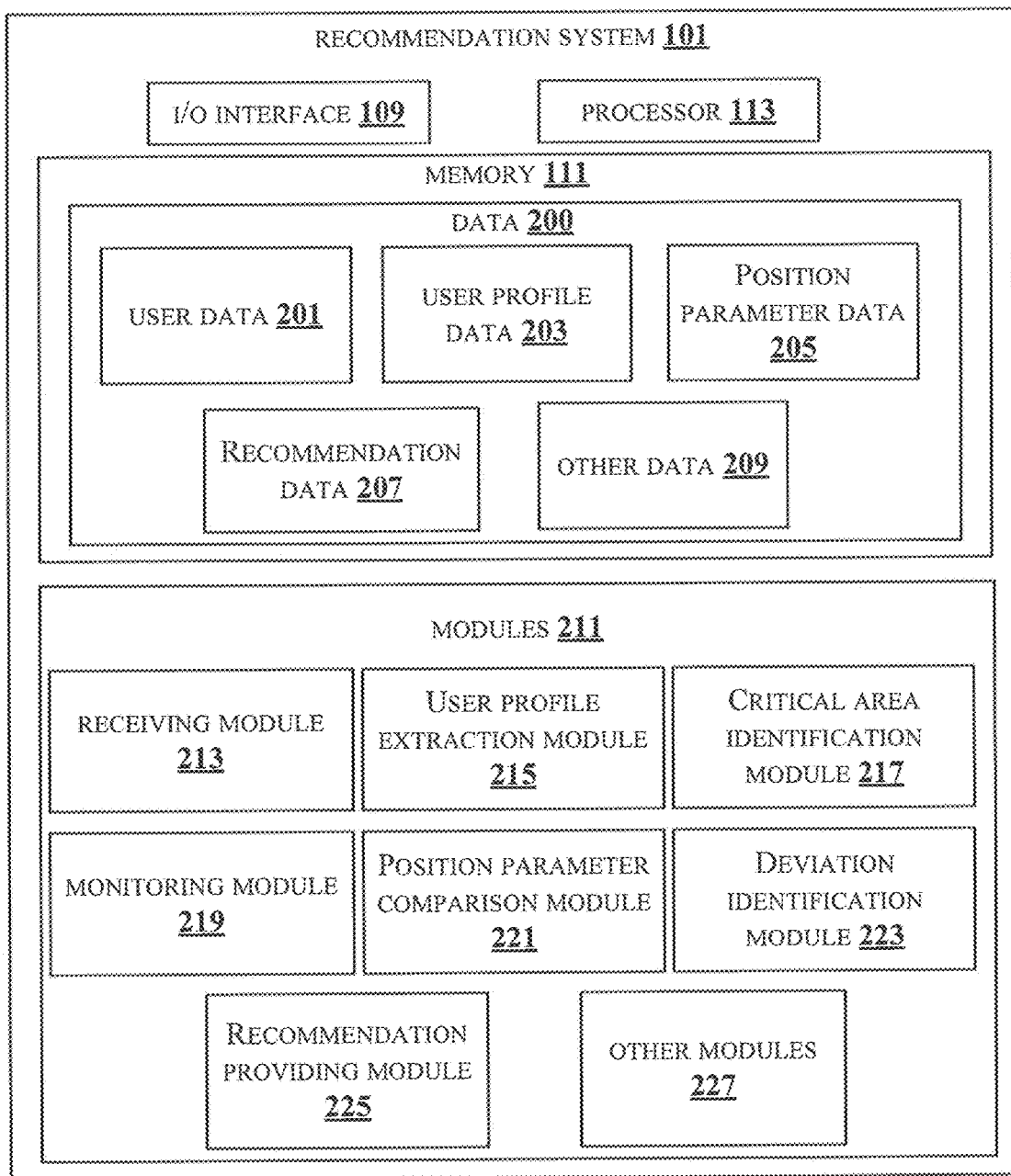
FIG. 2a shows a detailed block diagram of a recommendation system in accordance with some embodiments of the present disclosure.

FIG. 2a shows a detailed block diagram illustrating a recommendation system in accordance with some embodiments of the present disclosure.

One or more data 200 and one or more modules 211 of the recommendation system 103 are described herein in detail. In an embodiment, the one or more data 200 comprises user data 201, user profile data 203, position parameter data 205, recommendation data 207 and other data 209 for recommending an optimal ergonomic position for a user of a computing device 101.

The user data 201 comprises information about the one or more data associated with the user for identifying the users.

The user data 201 comprise at least one of user login data, video feed from a video capturing unit and facial feature information of the user extracted from the video. The user login data is received form the computing device 101 in case the user is a registered user.

The user profile data 203 comprises information about the profiles associated with the users of the computing device 101. In an embodiment, the user profile is generated at the time of registration of the user. The user profile comprises information of the user for example, user name, age, height and weight details, heath related data etc. Further, the user profile may also comprise information about any specific recommendations from a health specialist for any health related issues. For example, due to an injury in any of the critical areas like elbow, leg etc., the user is recommended to keep the position of the affected area at a specific posture.

The position parameter data 205 comprises information the plurality of pre-defined position parameters needed for optimal ergonomic position. The plurality of pre-defined position parameters comprise distance of the user's eye to the device display, height of the top edge of the device display relative to the eye level of the user, tilt angle of the device display, device display brightness, angle of the user's arms, elbow, wrist, head and neck, ambient lightning data, temperature data, sound level, humidity and position of the keyboard and mouse. Table 1 below shows exemplary and non-limiting values of the pre-defined plurality of pre-defined position parameters.

TABLE 1

| Sl. No | Pre-defined Position Parameter | Values |
|---|---|---|
| 1 | Distance from eyes to display surface | 20 to 40 inches |
| 2 | Height of the top edge of the display surface relative to the person's eye level | User's eye should be about 2 to 3 inches below the top edge of the monitor. The center of the monitor should be 15 to 20 degrees below the eye level |
| 3 | Tilt angle of the display | Monitor should be facing directly in front of the user. There should not be any tilt angle. |
| 4 | Brightness | Screen brightness is proportional to the ambient light |
| 5 | Angle of arm | Upper arm and elbow are as close to the body possible. |
| 6 | Angle of elbow | Greater than 90° |
| 7 | Angle of wrist | As flat as possible (Not bent up or down) |
| 8 | Head and Neck | Head and Neck are as straight as possible |
| 9 | Keyboard | User is centered on the keyboard |
| 10 | Mouse | Closure |

The recommendation data 207 comprises information about the recommendation to the users for correcting any deviations in any of the plurality of pre-defined position parameters. The recommendation data 207 comprise instructions for correcting the sitting posture of the user, change in the user arm and the user wrist positions, adjusting ambient light, temperature, humidity and sound level etc.

The other data 209 may comprise data, including temporary data and temporary files, generated by modules for performing the various functions of the recommendation system 103.

In an embodiment, the one or more data 200 in the memory 111 are processed by the one or more modules 211 of the recommendation system 103. As used herein, the term module refers to an application specific integrated circuit (ASIC), an electronic circuit, a field-programmable gate arrays (FPGA), Programmable System-on-Chip (PSoC), a combinational logic circuit, and/or other suitable components that provide the described functionality. The said modules when configured with the functionality defined in the present disclosure will result in a novel hardware.

In one implementation, the one or more modules 211 may include, for example, a receiving module 213, a user profile extraction module 215, critical area identification module 217, monitoring module 219, position parameter comparison module 221, deviation identification module 223 and recommendation providing module 225.

Figure 2B:
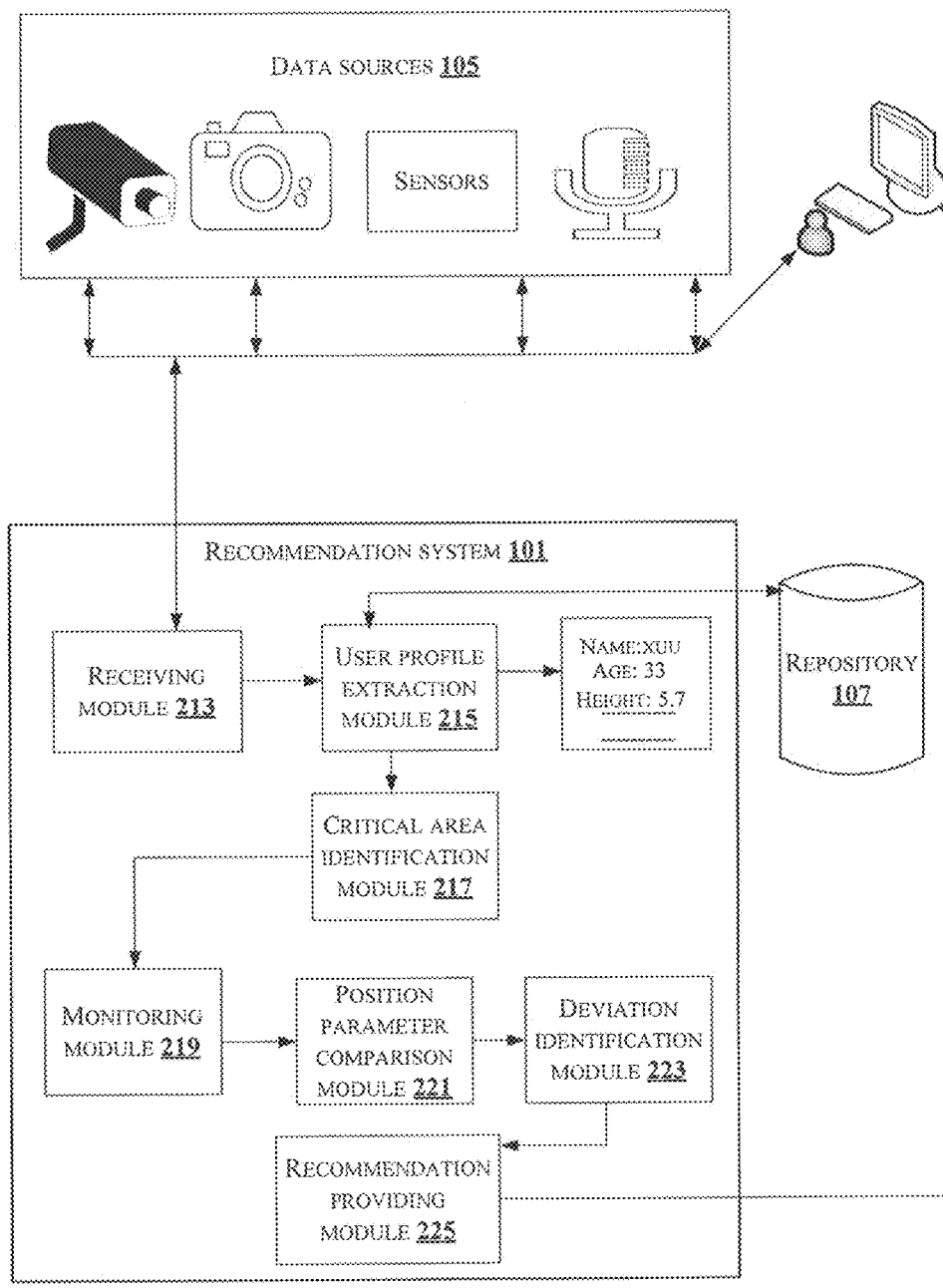
FIG. 2b shows an exemplary environment illustrating data flow between different modules of recommendation system in accordance with some embodiment of the present disclosure.

The one or more modules 211 may also comprise other modules 227 to perform various miscellaneous functionalities of the recommendation system 103. It will be appreciated that such aforementioned modules may be represented as a single module or a combination of different modules. FIG. 2b shows an exemplary environment illustrating data flow between different modules of recommendation system in accordance with some embodiment of the present disclosure.

The receiving module 213 receives the user data associated with a user from the one or more data sources 105. The user data are utilized for identifying a user. In an embodiment, the receiving module 213 may receive the user data from the computing device 101 in case the user data is login details of the user. Further, the user data such as facial features and video feed are received from the video capturing unit, cameras etc.

The user profile extraction module 215 extracts the profile of the user of the computing device 101. The user profile extraction module 215 extracts the profiles from the repository 107. The user profile are already generated and stored on the repository at the time of registration. In an embodiment, each of the user profile is stored in the repository 107 with a unique identifier of the user. The user profile extraction module 215 extracts the user profile based on the user data received. In an embodiment, if a new user is detected, the user profile extraction module 215 loads a default profile for the user, where the default profile is based on the pre-defined plurality of pre-defined position parameters. The below equation represent a set of profiles for users:

$$P(U)=\{p_i\}, i=\{1 \ldots n\} \quad (1)$$

Where, P denotes a profile for a user 'U' as a set of 'n' parameters.

The critical area identification module 217 identifies one or more critical areas of the user which are required to be monitored for ergonomic positions based on the extracted profile of the user and the user data. The critical areas are identified to determine if the user comprises any specific values for any of the position parameters. Table 2 below shows an example of user specific values for a particular user. In an embodiment, the critical areas of the user may comprise ears, nose, eyes, legs, wrist etc. The critical areas of the users are associated with the plurality of pre-defined parameters.

TABLE 2

| Sl. No | Parameter | User Specific Value |
|---|---|---|
| 1 | Distance from eyes to display surface | 30 inches |
| 2 | Height of the top edge of the display surface relative to the person's eye level | 3 inches below the top edge of the monitor |
| 3 | Tilt angle of the display | Monitor angle 5° |
| 4 | Brightness | 10 units |
| 5 | Angle of arm | Upper arm and elbow are as close to the body possible. |
| 6 | Angle of elbow | 95° |
| 7 | Angle of wrist | flat |
| 8 | Head & Neck | straight |
| 9 | Keyboard | Do not track |
| 10 | Mouse | Do not track |

The monitoring module 219 monitors each of the plurality of pre-defined position parameters of the user and also determine the corresponding values for each of the pre-defined position parameters of the user. In an embodiment, the values are determined by monitoring the sitting position of the user, ambient lightning of the environment, temperature, sound and humidity. The monitoring module 219 monitors the plurality of pre-defined positions parameters based on the output of the video capturing unit, depth sensors, light sensor, humidity sensor and temperature sensor. In an embodiment, the depth sensor along with a target illumination beam measures the direct distance from the display unit to the point in the user's body which is illuminated by the target beam in order to determine the viewing distance of the user. Further, based on the viewing distance measured and eye position detected from the user image, the eye level is calculated by mapping pixel coordinates to real world coordinates. The values of elbow and wrist position are also determined by depth sensor, which generates the skeletal profile of the user and angles of elbow and wrist joints are measured. The activity level of the user, which comprises movement of head, arms and wrist are tracked by the video capturing unit and depth sensor. Further, the light sensors measure the ambient lighting around the user and the sound level is measured by the microphone. The temperature and humidity around the user is measured by the temperature and humidity sensors respectively. The equation below shows measurements of temperature and humidity around the user:

$$M(U)=\{m_i\}, i=\{1 \ldots n\} \quad (2)$$

Where M=measurement for a user U as a set of 'n' parameters

The position parameter comparison module 221 compares the values of the plurality of pre-defined position parameters determined by the monitoring module 219 with the values of the pre-defined plurality of pre-defined position parameters. In an embodiment, the pre-defined plurality of pre-defined position parameters is the standard values set for any user. Further, the position parameter comparison module 221 compares the values of any of the pre-defined position parameter with specific user defined values, identified from the user profile, in case the user comprises any specific values for any of the plurality of pre-defined position parameter.

Figure 3:
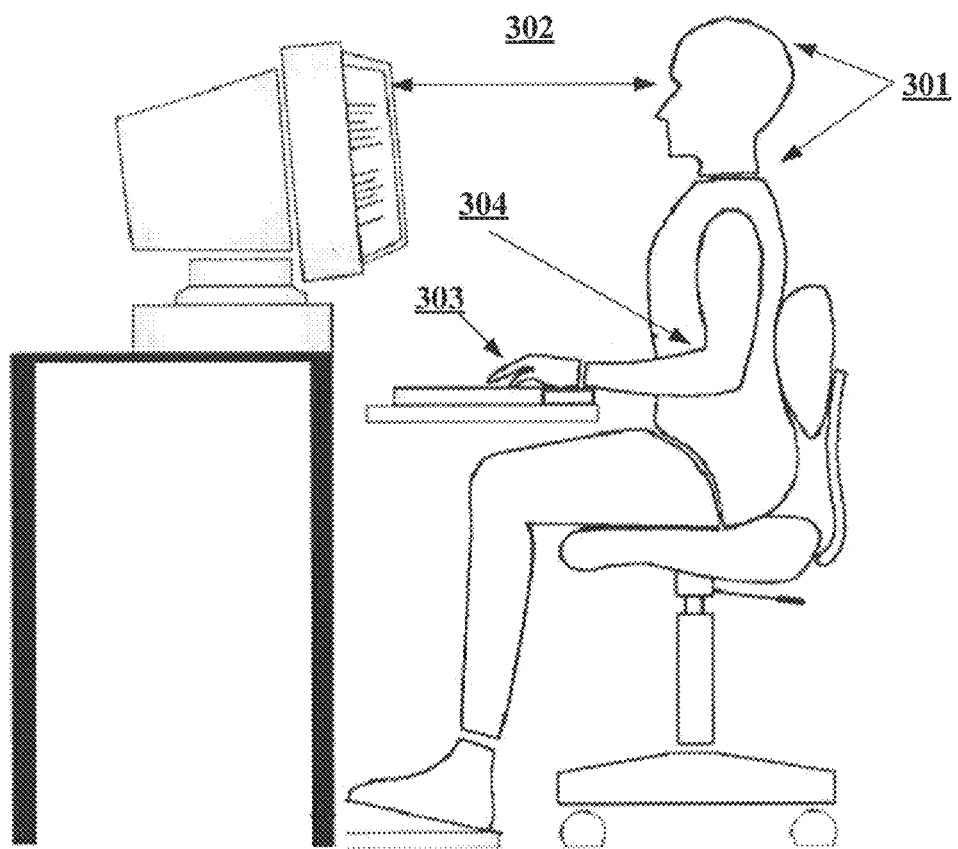
FIG. 3 shows an exemplary user illustrating optimal ergonomic posture in accordance with some embodiment of the present disclosure.

The deviation identification module 223 identifies any deviations in one or more of the plurality of pre-defined position parameters based on the output of the position parameter comparison module 221. The deviation identification module 223 identifies deviation, if the values of any of the plurality of pre-defined position parameter are outside an acceptable threshold range of the pre-defined plurality of pre-defined position parameters. For example, the pre-defined value for distance from eye to display unit is the range of 20 to 40 inches. In case, the distance from the eye to the display unit for a user is outside this range, a deviation in the distance of eye from display unit parameter is indicated. Further, the deviation identification module 223 provides deviation notification to the user based on the identification. The deviation notification comprises information about deviation in at least one of user posture, change in arms and wrist positions, ambient light, temperature, humidity and sound level. The equations below shows deviation and threshold value representations. FIG. 3b shows an exemplary deviated user ergonomic posture in accordance with some embodiment of the present disclosure.

$$D(U)=\{d_i|d_i=p_i-m_i\}, i=\{1 \ldots n\} \quad (3)$$

Where, D=deviations for a user 'U' as a set of 'n' parameters.

$$T(U)=\{t_i, v_i\}, i=\{1 \ldots n\} \quad (4)$$

Where 'T' denotes threshold for a user 'U' as a set of 'n' parameters and duration 'v.

Also, the condition for triggering a deviation notification N for user 'U' for parameters 'p' is shown in below equation:

$$N(U, p_i) = d_i > t_i \text{ for duration} > v_i, i=\{1 \ldots n\} \quad (5)$$

The recommendation providing module 225 provides recommendation to the user for correcting any deviations from the one or more of the plurality of pre-defined position parameter. The recommendation providing module 225 provides recommendation once a user is notified for any of the deviations. The deviation notification is provided in real-time visual, textual form, graphical form, and animated form and/or AV indication to the users on the computing device 101. Based on the type of deviation and the pre-defined parameter, the recommendation providing module 225 provides recommendation for correcting sitting posture adjusting the lighting and temperature, change in arms and wrist positions in case the notification is associated with the ergonomic positions. Further, in an embodiment, if the deviation notification is related to ambient lighting and temperature, the recommendation providing module 225 sends the control signals to the lighting and AC thermostat for adjusting automatically. Also, if the notification is related to the sound level and humidity, the user is notified and recommended accordingly. FIG. 3a shows an exemplary user optimal ergonomic posture in accordance with some embodiment of the present disclosure. As shown in FIG. 3a, a user is sitting in front of a computer device in an optimal position. The plurality of pre-defined parameters are indicated, where the position of head and neck is indicated by '301'. '302' indicates the distance of the user eye from the display unit, 303 indicates the angle of wrist and 304 indicate the angle of elbow.

Figure 4:
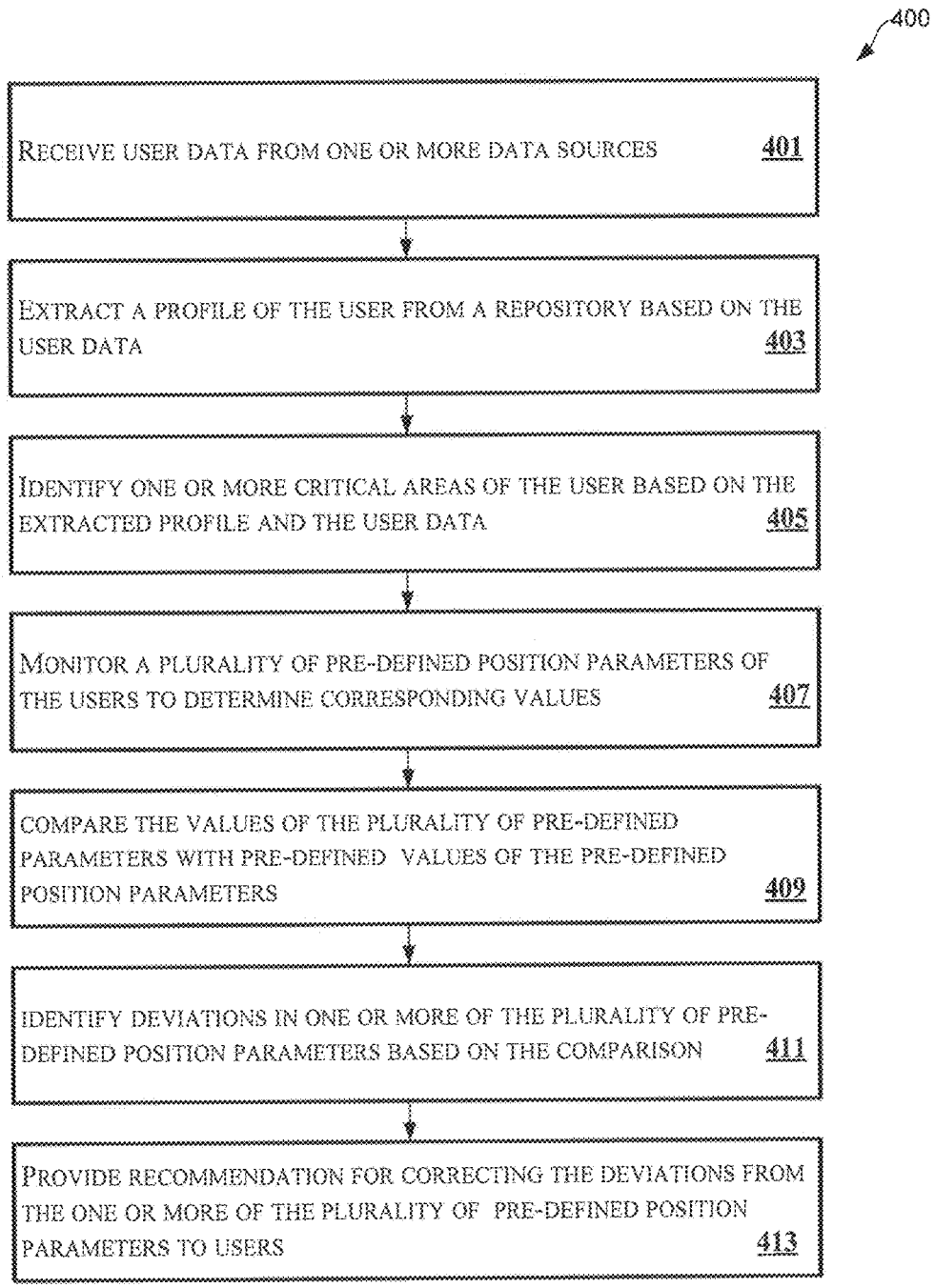
FIG. 4 illustrates a flowchart showing a method for recommending an optimal ergonomic position for a user of a computing device in accordance with some embodiments of present disclosure.

FIG. 4 illustrates a flowchart showing a method for recommending an optimal ergonomic position for a user of a computing device in accordance with some embodiments of present disclosure.

As illustrated in FIG. 4a, the method 400 comprises one or more blocks for recommending an optimal ergonomic position for a user of a computing device. The method 400 may be described in the general context of computer executable instructions. Generally, computer executable instructions can include routines, programs, objects, components, data structures, procedures, modules, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 401, the recommendation system 101 receives user data from one or more data sources.

At block 403, the recommendation system 101 extracts a profile of the user from a repository based on the user data.

At block 405, the recommendation system 101 identifies one or more critical areas of the user based on the extracted profile and the user data, where each of the one or more critical areas are associated with a plurality of pre-defined position parameters.

At block 407, the recommendation system 101 monitors the plurality of pre-defined position parameters of the users to determine corresponding value.

At block 409, the recommendation system 101 compares the values of the plurality of pre-defined position parameters with pre-defined values of the plurality of pre-defined position parameters.

At block 411, the recommendation system 101 identifies deviations in one or more of the plurality of position parameters based on the comparison.

At block 413, the recommendation system 101 provides recommendations for correcting the deviations from the one or more of the plurality of pre-defined position parameters to the users.

Computing System

Figure 5:
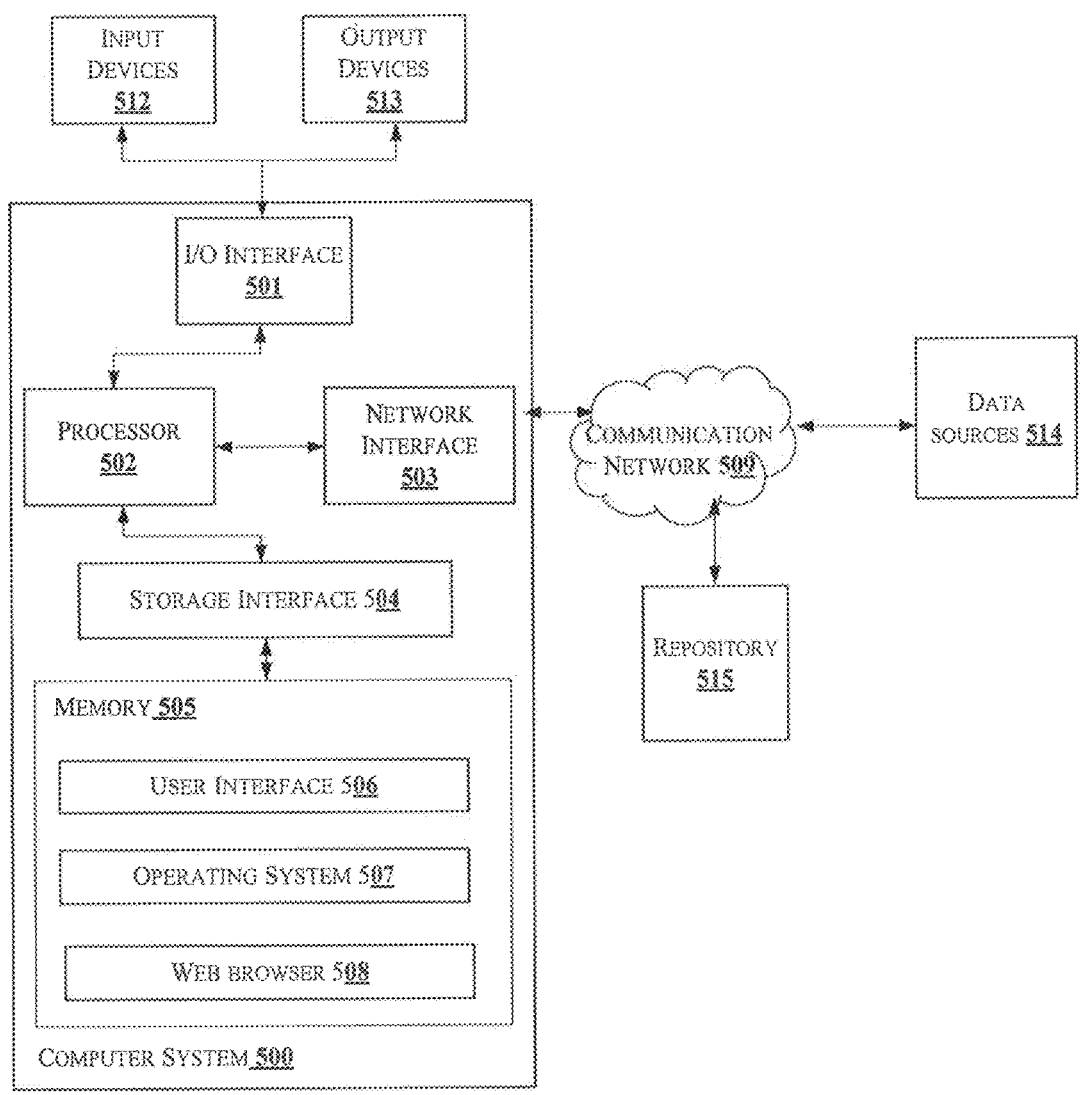
FIG. 5 illustrates a block diagram of an exemplary computer system for implementing embodiments consistent with the present disclosure.

FIG. 5 illustrates a block diagram of an exemplary computer system 500 for implementing embodiments consistent with the present disclosure. In an embodiment, the computer system 500 is used to implement the recommendation system. The computer system 500 may comprise a central processing unit ("CPU" or "processor") 502. The processor 502 may comprise at least one data processor for recommending optimal position for a user. The processor 502 may include specialized processing units such as integrated system (bus) controllers, memory management control units, floating point units, graphics processing units, digital signal processing units, etc.

The processor 502 may be disposed in communication with one or more input/output (I/O) devices (not shown) via I/O interface 501. The I/O interface 501 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 501, the computer system 500 may communicate with one or more I/O devices. For example, the input device may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 500 consists of a recommendation system. The processor 502 may be disposed in communication with the communication network 509 via a network interface 503. The network interface 503 may communicate with the communication network 509. The network interface 503 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 509 may include, without limitation, a direct interconnection, local area network (LAN), wide area network (WAN), wireless network (e.g., using Wireless Application Protocol), the Internet, etc. Using the network interface 503 and the communication network 509, the computer system 500 may communicate with data sources 514 and repository 515. The network interface 503 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 509 includes, but is not limited to, a direct interconnection, an e-commerce network, a peer to peer (P2P) network, local area network (LAN), wide area network (WAN), wireless network (e.g., using Wireless Application Protocol), the Internet, Wi-Fi and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 502 may be disposed in communication with a memory 505 (e.g., RAM, ROM, etc. not shown in FIG. 4) via a storage interface 504. The storage interface 504 may connect to memory 505 including, without limitation, memory drives, removable disc drives, etc., employing connection protocols such as serial advanced technology attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 505 may store a collection of program or database components, including, without limitation, user interface 506, an operating system 507, web browser 508 etc. In some embodiments, computer system 500 may store user/application data 506, such as the data, variables, records, etc., as described in this disclosure. Such databases may be implemented as fault-tolerant, relational, scalable, secure databases such as Oracle or Sybase.

The operating system 507 may facilitate resource management and operation of the computer system 500. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like.

In some embodiments, the computer system 500 may implement a web browser 508 stored program component. The web browser 508 may be a hypertext viewing application, such as Microsoft Internet Explorer, Google Chrome, Mozilla Firefox, Apple Safari, etc. Secure web browsing may be provided using Secure Hypertext Transport Protocol (HTTPS), Secure Sockets Layer (SSL), Transport Layer Security (TLS), etc. Web browsers 508 may utilize facilities such as AJAX, DHTML, Adobe Flash, JavaScript, Java, Application Programming Interfaces (APIs), etc. In some embodiments, the computer system 500 may implement a mail server stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 500 may implement a mail client stored program component. The mail client may be a mail viewing application, such as Apple Mail, Microsoft Entourage, Microsoft Outlook, Mozilla Thunderbird, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

An embodiment of the present disclosure recommends an efficient and optimal ergonomic position for a user.

An embodiment of the present disclosure provides user specific customizable profiles which comprise complete details of the user. This helps in determining optimal ergonomic position as per user condition.

The present disclosure provides an automatic control of the display parameters, lighting and temperature for effective user requirement.

An embodiment of the present disclosure help in avoiding any health related issues associated with the computing device based on the recommendations provided.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs. DRAMs, SRAMs, Flash Memory, firmware, programmable logic, etc.), etc. Further, non-transitory computer-readable media comprise all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices. An "article of manufacture" comprises non-transitory computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the invention, and that the article of manufacture may comprise suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 5 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Environment |
| 101 | computing device |
| 103 | Recommendation system |
| 105 | Data sources |
| 107 | Repository |
| 109 | I/O interface |
| 111 | Memory |
| 113 | Processor |
| 200 | Data |
| 201 | User data |
| 203 | User profile data |
| 205 | Position parameter data |
| 207 | Recommendation data |
| 209 | Other data |
| 211 | Modules |
| 213 | Receiving module |
| 215 | User profile extraction module |
| 217 | Critical area identification module |
| 219 | Monitoring module |
| 221 | Position parameter comparison module |
| 223 | Deviation identification module |
| 225 | Recommendation providing module |
| 227 | Other modules |

What is claimed is:

1. A method for recommending an optimal ergonomic position for a user of a computing device, the method comprising:
receiving, by a recommendation system, user data from one or more data sources;

extracting, by the recommendation system, a profile of the user from a repository based on the user data;

identifying, by the recommendation system, one or more critical areas of the user based on the extracted profile and the user data, wherein each of the one or more critical areas are associated with a plurality of pre-defined position parameters;

monitoring, by the recommendation system, the plurality of pre-defined position parameters of the user to determine corresponding values;

comparing, by the recommendation system, pre-defined values of the plurality of pre-defined position parameters with determined corresponding values of the pre-defined position parameters and with specific user defined values identified from the profile of the user, wherein the specific user defined values are pre-defined for the user for at least one of the plurality of pre-defined position parameters;

identifying, by the recommendation system, deviations in values of one or more of the plurality of pre-defined position parameters from a threshold range based on the comparison, over a time duration; and providing, by the recommendation system, one or more recommendations for correcting the deviations to the user.

2. The method as claimed in claim 1, wherein the user data of the user comprises at least one of user login data, video feed from a video capturing unit, or facial feature information of the user.

3. The method as claimed in claim 1, wherein the one or more data sources comprises a video capturing unit, a depth sensor, a light sensor, a microphone, a humidity sensor, or a temperature sensor.

4. The method as claimed in claim 1, wherein the pre-defined values of the pre-defined position parameters comprises at least one of user defined values and pre-defined recommendation values.

5. The method as claimed in claim 1,
wherein the pre-defined position parameters comprises distance of a user eye to a device display unit, height of top edge of the device display unit relative to eye level of the user, tilt angle of the device display unit, device display unit brightness, angle of the user's arms, elbow, wrist, head and neck, ambient lighting data, temperature data, sound level, humidity, and position of keyboard and mouse;
wherein identifying deviations in one or more of the plurality of pre-defined position parameters based on the comparison further comprises determining a duration for which the one or more of the plurality of pre-defined position parameters exceeds a corresponding threshold; and
wherein providing one or more recommendations for correcting the deviations to the user is based on the identified deviations and the determined duration.

6. The method as claimed in claim 1, further comprising providing the one or more recommendations for correcting the deviations to the user comprising information about at least one deviations of user posture, ambient lighting, temperature, sound level, or humidity.

7. The method as claimed in claim 1, wherein the one or more recommendations comprises instructions for correcting sitting posture, change in user arm and wrist positions, and adjusting ambient light, temperature, humidity, or sound level.

8. A recommendation system for recommending optimal ergonomic position for a user of a computing device comprising:
a processor; and
a memory communicatively coupled to the processor, wherein the memory stores processor instructions, which, on execution, causes the processor to:
receive user data from one or more data sources;
extract a profile of the user from a repository based on the user data;
identify one or more critical areas of the user based on the extracted profile and the user data, wherein each of the one or more critical areas are associated with a plurality of pre-defined position parameters;
monitor the plurality of pre-defined position parameters of the user to determine corresponding values;
compare pre-defined values of the plurality of pre-defined position parameters with determined corresponding values of the pre-defined position parameters and with specific user defined values identified from the profile of the user, wherein the specific user defined values are pre-defined for the user for at least one of the plurality of pre-defined position parameters;
identify deviations in values of one or more of the plurality of pre-defined position parameters from a threshold range based on the comparison, over a time duration; and
provide one or more recommendations for correcting the deviations to the user.

9. The recommendation system as claimed in claim 8, wherein the user data of the user comprises at least one of user login data, video feed from a video capturing unit, or facial feature information of the user.

10. The recommendation system as claimed in claim 8, wherein the one or more data sources comprises a video capturing unit, a depth sensor, a light sensor, a microphone, a humidity sensor, or a temperature sensor.

11. The recommendation system as claimed in claim 8, wherein the pre-defined values of the pre-defined position parameters comprises at least one of user defined values and pre-defined recommendation values.

12. The recommendation system as claimed in claim 8,
wherein the pre-defined position parameters comprises distance of a user eye to a device display unit, height of top edge of the device display unit relative to eye level of the user, tilt angle of the device display unit, device display unit brightness, angle of the user's arms, elbow, wrist, head and neck, ambient lighting data, temperature data, sound level, humidity, or position of keyboard and mouse;
wherein identifying deviations in one or more of the plurality of pre-defined position parameters based on the comparison further comprises determining a duration for which the one or more of the plurality of pre-defined position parameters exceeds a corresponding threshold; and
wherein providing one or more recommendations for correcting the deviations to the user is based on the identified deviations and the determined duration.

13. The recommendation system as claimed in claim 8, further comprising providing the one or more recommendations for correcting the deviations to the user comprising information about at least one of deviations of user posture, ambient lighting, temperature, sound level, or humidity.

14. The recommendation system as claimed in claim 8, wherein the one or more recommendations comprises instructions for correcting sitting posture, change in user arm and wrist positions, and adjusting ambient light, temperature, humidity, and sound level.

15. A non-transitory computer readable medium including instruction stored thereon that when processed by at least one processor cause a recommendation system to perform operation comprising:
receiving user data from one or more data sources:
extracting a profile of the user from a repository based on the user data;
identifying one or more critical areas of the user based on the extracted profile and the user data, wherein each of the one or more critical areas are associated with a plurality of pre-defined position parameters;
monitoring the plurality of pre-defined position parameters of the user to determine corresponding values;
comparing pre-defined values of the plurality of pre-defined position parameters with determined corresponding values of the pre-defined position parameters and with specific user defined values identified from the profile of the user, wherein the specific user defined values are pre-defined for the user for at least one of the plurality of pre-defined position parameters;
identifying deviations in values of one or more of the plurality of pre-defined position parameters from a threshold range based on the comparison, over a time duration; and
providing one or more recommendations for correcting the deviations to the user.

16. The medium as claimed in claim 15, wherein the user data of the user comprises at least one of user login data, video feed from a video capturing unit, or facial feature information of the user.

17. The medium as claimed in claim 15, wherein the one or more data sources comprises a video capturing unit, a depth sensor, a light sensor, a microphone, a humidity sensor, or a temperature sensor.

18. The medium as claimed in claim 15, wherein the pre-defined values of the pre-defined position parameters comprises at least one of user defined values and pre-defined recommendation values.

19. The medium as claimed in claim 15,
wherein the pre-defined position parameters comprises distance of a user eye to a device display unit, height of top edge of the device display unit relative to eye level of the user, tilt angle of the device display unit, device display unit brightness, angle of the user's arms, elbow, wrist, head and neck, ambient lighting data, temperature data, sound level, humidity, or position of keyboard and mouse;
wherein identifying deviations in one or more of the plurality of pre-defined position parameters based on the comparison further comprises determining a duration for which the one or more of the plurality of pre-defined position parameters exceeds a corresponding threshold; and
wherein providing one or more recommendations for correcting the deviations to the user is based on the identified deviations and the determined duration.

20. The medium as claimed in claim 15 further comprising providing the one or more recommendations for correcting the deviations to the user comprising information about at least one of deviations of user posture, ambient lighting, temperature, sound level, or humidity.

21. The medium as claimed in claim 15, wherein the one or more recommendations comprises instructions for correcting sitting posture, change in user arm and wrist positions, and adjusting ambient light, temperature, humidity, and sound level.

* * * * *